United States Patent
Han et al.

(10) Patent No.: US 10,173,967 B2
(45) Date of Patent: Jan. 8, 2019

(54) AZO MONOMER, AND AZO POLYMER PREPARED BY POLYMERIZATION OF AZO MONOMER

(71) Applicants: LG Chem, Ltd., Seoul (KR); IUCF-HYU (Industry-University Cooperation Foundation Hanyang University), Seoul (KR)

(72) Inventors: Yang Kyoo Han, Seoul (KR); In-Joon Byun, Incheon (KR); Sung Soo Yoon, Daejeon (KR); Je Gwon Lee, Daejeon (KR)

(73) Assignees: LG Chem, Ltd. (KR); IUCF-HYU (Industry-University Cooperation Foundation Hanyang University) (KR)

( * ) Notice: Subject to any disclaimer, the term of this patent is extended or adjusted under 35 U.S.C. 154(b) by 0 days.

(21) Appl. No.: 15/518,679

(22) PCT Filed: Dec. 2, 2015

(86) PCT No.: PCT/KR2015/013080
§ 371 (c)(1),
(2) Date: Apr. 12, 2017

(87) PCT Pub. No.: WO2016/104982
PCT Pub. Date: Jun. 30, 2016

(65) Prior Publication Data
US 2017/0240504 A1    Aug. 24, 2017

(30) Foreign Application Priority Data

Dec. 22, 2014  (KR) .................. 10-2014-0186250
Dec. 1, 2015   (KR) .................. 10-2015-0169806

(51) Int. Cl.
C07C 245/08    (2006.01)
C08F 20/34     (2006.01)
(Continued)

(52) U.S. Cl.
CPC ............ *C07C 245/08* (2013.01); *C08F 20/34* (2013.01); *C08F 120/36* (2013.01); *G01N 33/20* (2013.01); *G01N 33/1813* (2013.01)

(58) Field of Classification Search
CPC ...... C07C 245/08; C08F 120/36; G01N 33/20
(Continued)

(56) References Cited

U.S. PATENT DOCUMENTS 4,504,368 A    3/1985   Delton et al.
5,466,496 A    11/1995  Jin
(Continued)

FOREIGN PATENT DOCUMENTS

JP    H0627720 B2    4/1994
JP    2001189166 A   7/2001
(Continued)

OTHER PUBLICATIONS

International Search Report from PCT/KR2015/013080, dated Feb. 23, 2016.
(Continued)

*Primary Examiner* — William K Cheung
(74) *Attorney, Agent, or Firm* — Lerner, David, Littenberg, Krumholz & Mentlik, LLP

(57) ABSTRACT

According to one embodiment of the present invention, an azo polymer forms a complex with a lithium ion and a sodium ion among alkali metal ions, but does not form a complex with a potassium ion. Therefore, the azo polymer is expected to be utilized as a material for a sensor capable of selectively detecting a specific alkali metal ion, or as a novel material capable of selectively trapping a specific alkali metal ion from a solution in which metal ions are mixed.

10 Claims, 7 Drawing Sheets

(51) Int. Cl.
    *G01N 33/20* (2006.01)
    *C08F 120/36* (2006.01)
    *G01N 33/18* (2006.01)

(58) Field of Classification Search
    USPC .............................................. 526/317.1, 346
    See application file for complete search history.

(56) References Cited

U.S. PATENT DOCUMENTS

| | | |
|---|---|---|
| 6,509,122 B1 | 1/2003 | Oyama |
| 2001/0033974 A1 | 10/2001 | Gavelin et al. |
| 2009/0286005 A1 | 11/2009 | Oki et al. |
| 2012/0116024 A1 | 5/2012 | Lyoda et al. |
| 2015/0159058 A1* | 6/2015 | Akiyama ............... C09J 133/14 156/247 |

FOREIGN PATENT DOCUMENTS

| | | | |
|---|---|---|---|
| JP | 2002-167370 | * | 6/2002 |
| JP | 2002167370 A | | 6/2002 |
| JP | 2003327729 A | | 11/2003 |
| JP | 2007131707 A | | 5/2007 |
| JP | 4741140 B2 | | 8/2011 |
| JP | 5224903 B2 | | 7/2013 |
| JP | 2014141711 A | | 8/2014 |
| KR | 100809835 B1 | | 3/2008 |
| KR | 101273823 B1 | | 6/2013 |
| KR | 1020140092973 A | | 7/2014 |
| WO | 2010137374 A1 | | 12/2010 |
| WO | 2013168712 A1 | | 11/2013 |

OTHER PUBLICATIONS

Natansohn, and Rochon, P., Photoinduced Motions in Azo-Containing Polymers, Chemical Reviews, Oct. 17, 2002, pp. 4139-4175, vol. 102, No. 11, American Chemical Society.

Han, Y.K. et al., Synthesis and Characterization of New Liquid-Crystalline Block Copolymers with p-Cyanoazobenzene Moieties and Poly(n-butyl acrylate) Segments Using Atom-Transfer Radical Polymerizaiton, Macromolecules, Nov. 6, 2004, pp. 9355-9365, vol. 37, No. 25, American Chemical Society.

Singh, A., Metal Ion Induced Phase Changes in Self-Assembled Membranes, Langmuir, Feb. 28, 1992, pp. 1570-1577, vol. 8, No. 6, American Chemical Society.

Harootunian et al., Fluorescence Ratio Imaging of Cytosolic Free Na+ in Individual Fibroblasts and Lymphocytes, The Journal of Biological Chemistry, Nov. 15, 1989, pp. 19458-19467, vol. 264, No. 32, The American Society for Biochemistry and Molecular Biology, Inc.

De Silva, et al., A molecular photoionic AND gate based on fluorescent signalling, Nature, Jul. 1, 1993, pp. 42-44, vol. 364, Nature Publishing Group.

Lee, et al., Regioselective Complexation of Metal Ion in Chromogenic Calix[4]biscrowns, J. Org. Chem., Mar. 13, 2004, pp. 2902-2905, vol. 69, No. 8, American Chemical Society.

Shen, et al., A Long Wavelength Fluorescent Hydrophilic Copolymer Based on Naphthalenediimide as pH Sensor with Broad Linear Response Range, Macromolecules, Jun. 22, 2011, pp. 5612-5618, vol. 44, American Chemical Society.

Ho et al., Synthesis of Upper-Rim Allyl- and p-Methoxyphenylazocalix[4]arenes and Their Efficiencies in Chromogenic Sensing of Hg2+ Ion, J. Org. Chem., Mar. 9, 2007, pp. 2434-2442, vol. 72, American Chemical Society.

Parlier, et al., An intramolecular journey of a carboxyl group around 1,2-dihydropyridines: multisite d- versus c-actonization reactions, Tetrahedron Letters, Oct. 31, 2009, pp. 7274-7279, vol. 50, Elsevier Ltd.

Wang, J. and Ha, C.S., A colorimetric and fluorescent turn-on chemosensor for Zn2þ based on an azobenzene-containing compound, Tetrahedron, Jun. 18, 2009, pp. 6959-6964, vol. 65, Elsevier Ltd.

Han, M. and Hara, M., Intense Fluorescence from Light-Driven Self-Assembled Aggregates of Nonionic Azobenzene Derivative, J. Am. Chem. Soc., Jul. 16, 2005, pp. 10951-10955, vol. 127, No. 31, American Chemical Society.

Wu, et al, Photoinduced Chirality in Thin Films of Achiral Polymer Liquid Crystals Containing Azobenzene Chromophores, Macromolecules, Aug. 11, 2004, pp. 6801-6805, vol. 37, No. 18, American Chemical Society.

Zhang et al., Synthesis and Photoresponsive Behaviors of Well-Defined Azobenzene-Containing Polymers via RAFT Polymerization, Macromolecules, Jun. 16, 2007, pp. 4809-4817, vol. 40, No. 14, American Chemical Society.

Smitha, P. and Asha, S.K., Structure Control for Fine Tuning Fluorescence Emission from Side-Chain Azobenzene Polymers, J. Phys. Chem. B, May 23, 2007, pp. 6364-6373, vol. 111, No. 23, American Chemical Society.

Ding, et al., Structure of self-assembled n-dodecyl substituted azobenzene poly(phenylene) dendrimers on graphite, J. Mater. Chem., Jul. 20, 2005, pp. 3431-3436, vol. 15, The Royal Society of Chemistry.

Ding et al, "Controlled synthesis of azobenzene functionalized homo and copolymers via direct acyclic diene metathesis polymerization", Polymer, Feb. 14, 2014, vol. 55, No. 7, pp. 1681-1687.

* cited by examiner

[Figure 1]
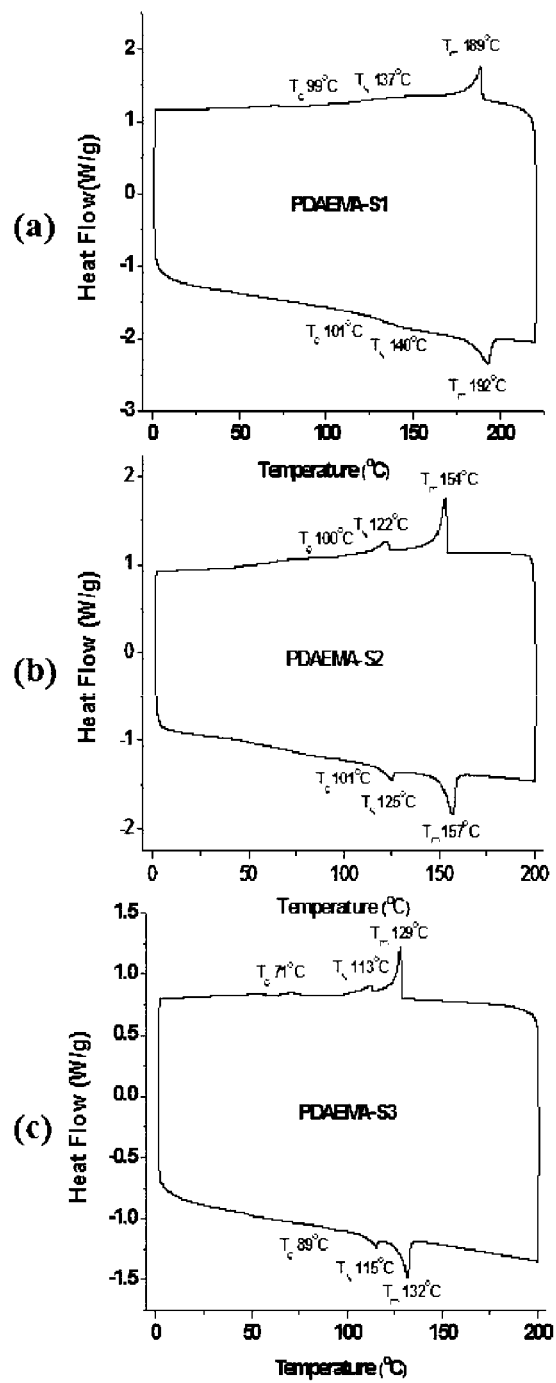

[Figure 2]
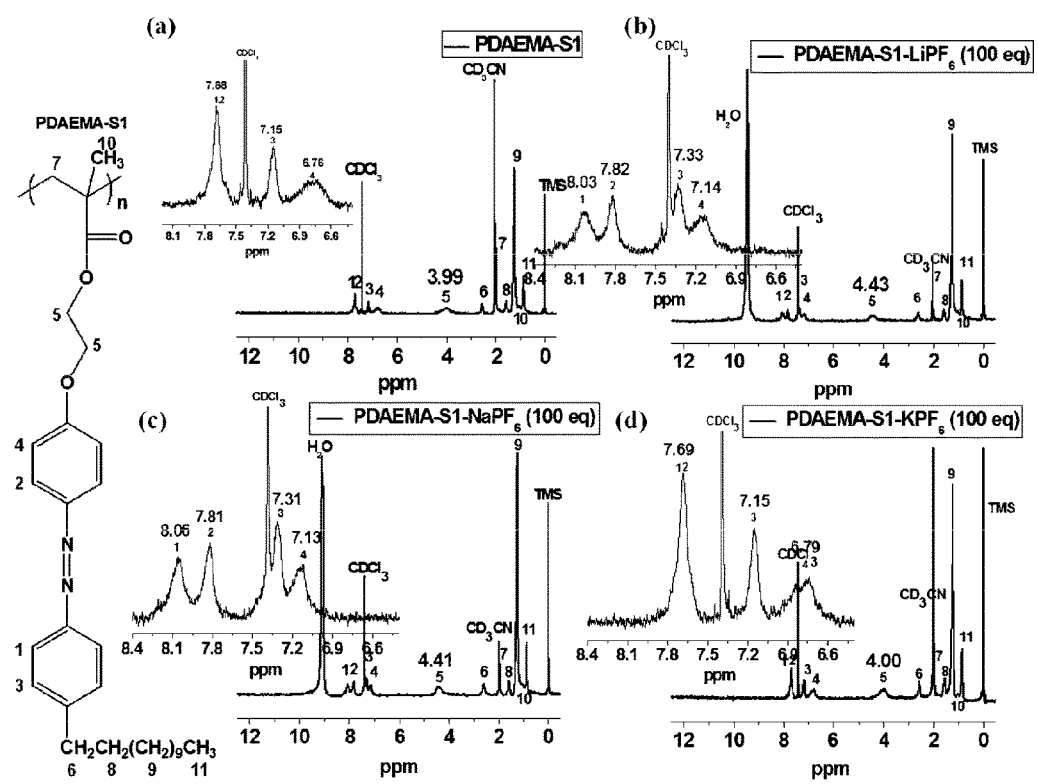

【Figure 3】
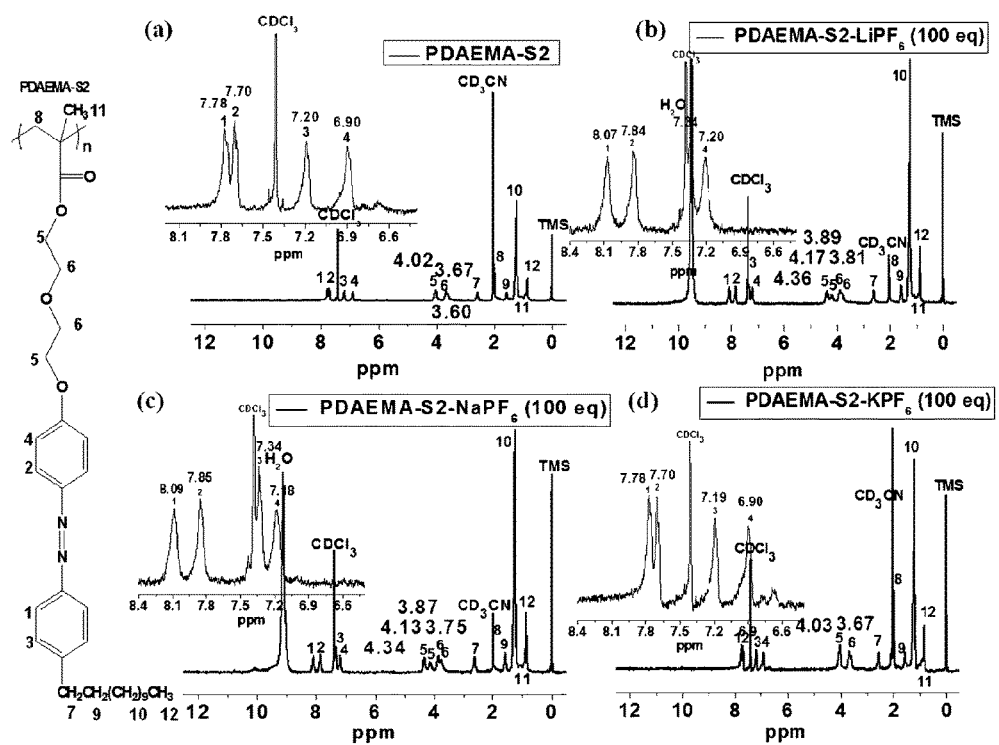

【Figure 4】
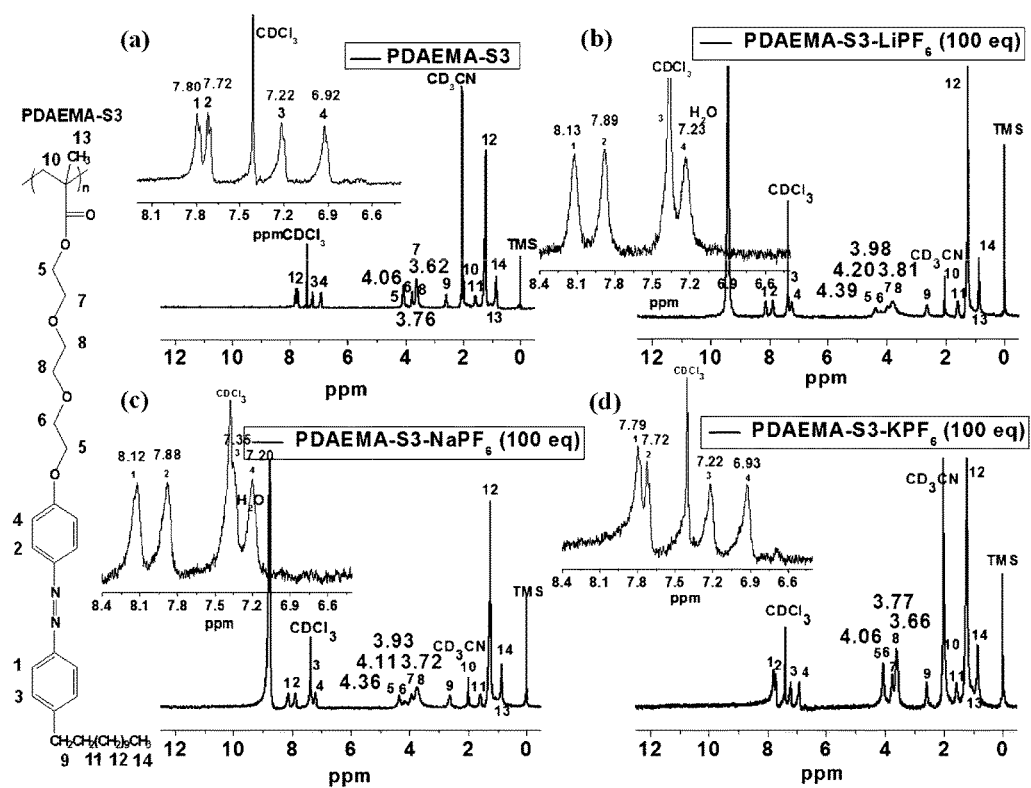

[Figure 5]
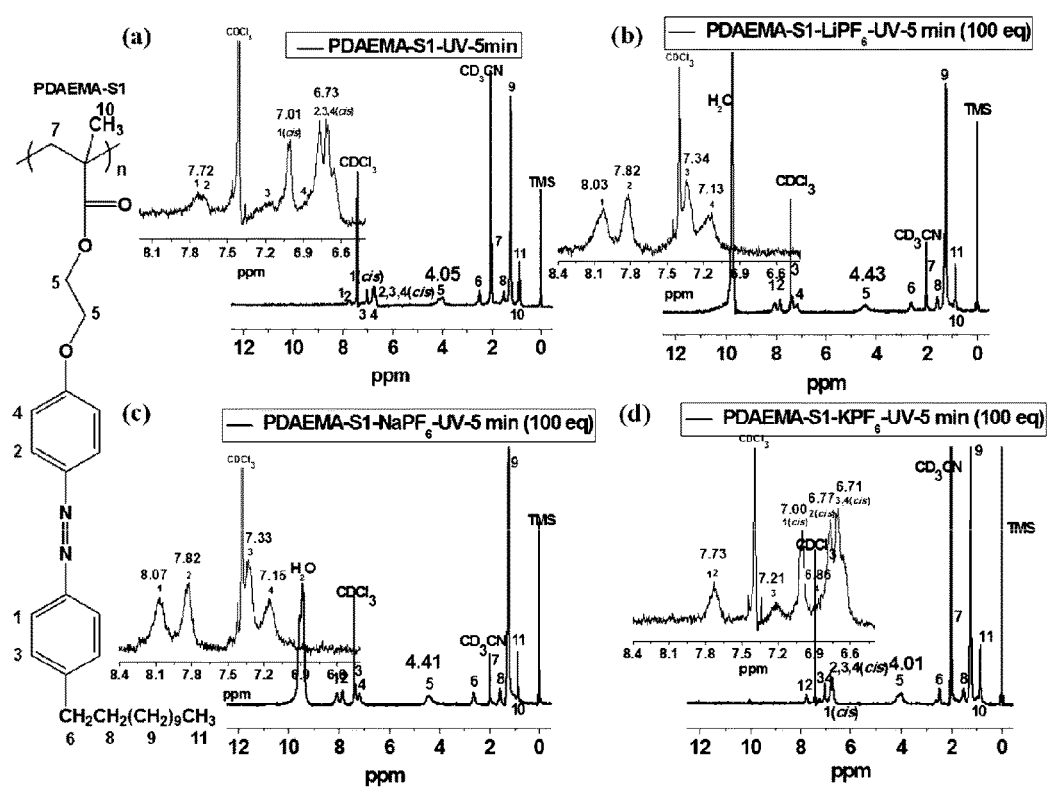

[Figure 6]
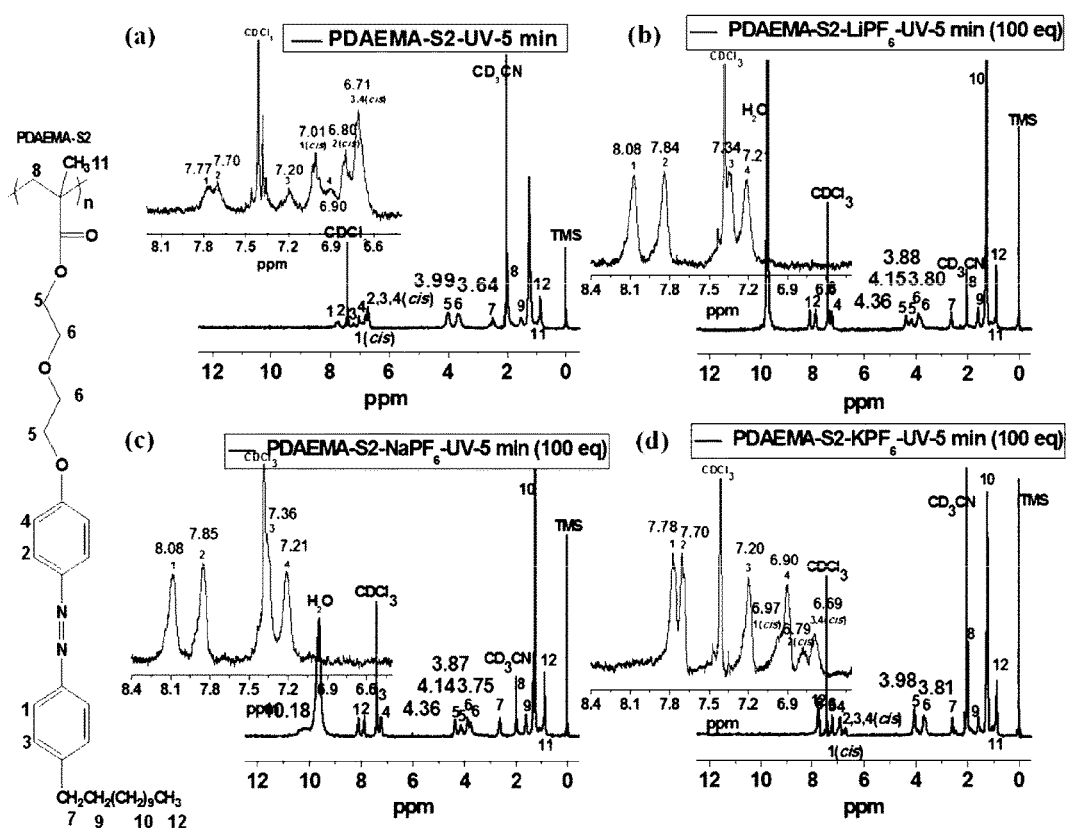

[Figure 7]
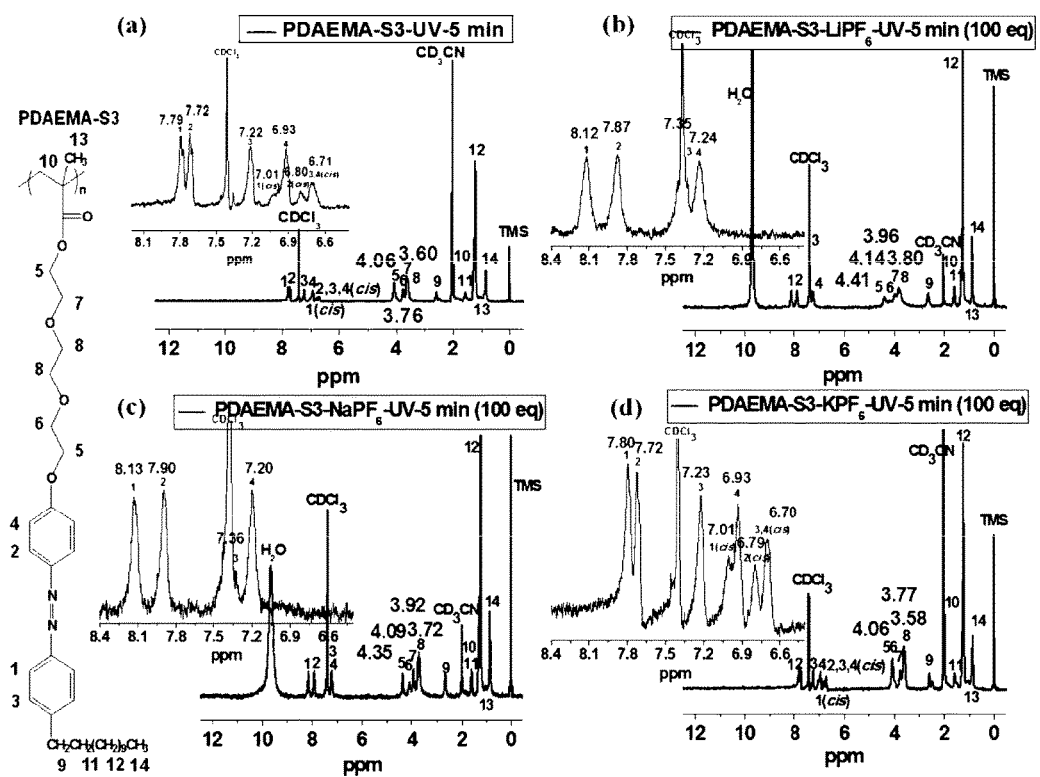

AZO MONOMER, AND AZO POLYMER PREPARED BY POLYMERIZATION OF AZO MONOMER

CROSS REFERENCE TO RELATED APPLICATION(S)

The present application is a national phase entry under 35 U.S.C. § 371 of International Application No. PCT/KR2015/013080, filed Dec. 2, 2015, published in Korean, which claims priority from Korean Patent Application No. 10-2014-0186250 filed on Dec. 22, 2014 and Korean Patent Application No. 10-2015-0169806 filed on Dec. 1, 2015 all of which are hereby incorporated by reference.

TECHNICAL FIELD

The present invention relates to azomonomer with a novel structure, azopolymer prepared by the polymerization thereof, and metal ion sensor and capturing agent applying the new characteristic of the azopolymer.

BACKGROUND

Recently, rechargeable secondary batteries using alkali metal cations are receiving focused attention as a clean energy source. Particularly, secondary batteries using a lithium ion have relatively low energy density, but has excellent oxidation stability, excellent solubility with an electrolyte solution and processibility, and thus, are widely used as advanced electronic products such as a PC, a display, a smart phone, etc. and batteries for supplying energy of automobiles. However, they are expensive and have limited reserves, and thus, the supply is limited. In order to solve such a problem of lithium ion batteries, development of next generation secondary batteries using metal ions with very high energy density such as sodium(Na), potassion(K), calcium(Ca), etc. is being actively progressed.

Besides, sodium and potassium cations control ion transport and action potential of cells in a lipid bilayer as well as physiological metabolism of organism, thus performing physiologically very important functions such as controlling of neural signal transmission, muscle contraction, and heart function, etc. (see Non-Patent Documents 1 and 2).

Thus, if a chemical sensor or separation membrane capable of selectively detecting alkali metal ions to control or separate is developed, the battery functions of the above explained secondary batteries may be improved and the energy density may be optimized, and various physiological functions can be more efficiently controlled.

Meanwhile, for use as a chemical sensor of alkali or transition metals, organic molecules or polymer materials into which a functional group capable of detecting and capturing metal ions should be used as a substrate of the sensor. As the molecules exhibiting such a sensor function, crown ether (see Non-Patent Documents 3 to 5), calixarene (see Non-Patent Documents 6 to 8) or unimolecular derivatives of azobenzene (see Non-Patent Document 9) have been mainly reported. Particularly, among these functional molecules, azobenzene has advantages of causing minute optical changes by photoisomerization such as changes in birefringence, absorptivity of complex and absorption wavelength. Thus, in order to use such optical properties, azopolymers into which an azobenzene group is introduced have been widely studied (see Non-Patent Documents 10 to 12). However, despite the above-described various advantages, azo-based monomers and polymers exhibiting the functions for detecting alkali metal or transition metal ions, and the properties and applications of these materials as a sensor material have been scarcely studied.

PRIOR ART

Non-Patent Document (Non-Patent Document 1) J. Biol. Chem., 1989, 264, 19458
(Non-Patent Document 2) Nature, 1993, 364, 42
(Non-Patent Document 3) J. L. Atwood, J. M. Lehn, Comprehensive Supramolecular Chemistry, 1$^{st}$ Ed., Pergamon, Oxford, UK, 1996
(Non-Patent Document 4) J. Org. Chem., 2004, 69, 2902
(Non-Patent Document 5) Macromolecules 2011, 44, 5612
(Non-Patent Document 6) J. Org. Chem., 2007, 72, 2434
(Non-Patent Document 7) Tetrahedron Letters, 2007, 48, 7274;
(Non-Patent Document 8) Tetrahedron, 2009, 65, 6959
(Non-Patent Document 9) J. AM. CHEM. SOC., 2005, 127, 10951
(Non-Patent Document 10) Chem. Rev., 2002, 102, 4139
(Non-Patent Document 11) Macromolecules, 2004, 37, 6801
(Non-Patent Document 12) Macromolecules, 2007, 40, 4809

DISCLOSURE

Technical Problem

It is an object of the present invention to provide azomonomer with a novel structure and azopolymer prepared by the polymerization thereof.

It is another object of the present invention to provide metal ion sensor and capturing agent applying the new characteristic of the azopolymer.

Technical Solution

According to one embodiment of the present invention, azomonomer represented by the following Chemical Formula 1 is provided.

[Chemical Formula 1]

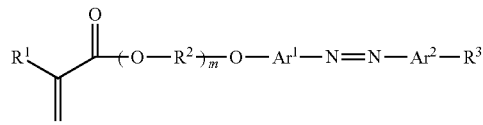

in the Chemical Formula 1, $R^1$ is hydrogen or a methyl group,
$R^2$ is an alkylene group having 1 to 4 carbon atoms,
$R^3$ is an alkyl group having 8 to 18 carbon atoms,
each of $Ar^1$ and $Ar^2$ is independently an arylene group having 6 to 12 carbon atoms, and
m is an integer of 1 to 5.

For example, in the Chemical Formula 1, $R^2$ may be an 1,2-ethylene group. And, $Ar^1$ and $Ar^2$ may be phenylene groups. $R^3$ may be an alkyl group having 10 to 16 carbon atoms.

Meanwhile, according to another embodiment of the present invention, azopolymer comprising a repeat unit represented by the following Chemical Formula 2 is provided.

[Chemical Formula 2]

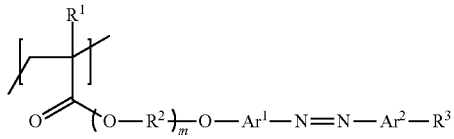

in the Chemical Formula 2, $R^1$ is hydrogen or a methyl group, $R^2$ is an alkylene group having 1 to 4 carbon atoms, $R^3$ is an alkyl group having 8 to 18 carbon atoms, each of $Ar^1$ and $Ar^2$ is independently an arylene group having 6 to 12 carbon atoms, and m is an integer of 1 to 5.

The azopolymer may have a number average molecular weight of 10,000 to 50,000 g/mol, and a molecular weight distribution of 1.2 to 4.0, and as the result, it can selectively bond to specific metal ions, and exhibit excellent light sensitivity.

And, the azopolymer may have a glass transition temperature of 60° C. to 120° C., a nematic liquid crystalline transition temperature of 90° C. to 160° C., and a melting point of 110° C. to 210° C. As the result, the azopolymer may exhibit excellent heat resistance.

Meanwhile, according to still another embodiment of the present invention, a metal ion sensor and a metal ion capturing agent using the azopolymer are provided.

The metal ion sensor and the metal ion capturing agent may be used for selectively detecting or separating lithium ions, sodium ions or a mixture thereof, particularly.

Effect of the Invention

The azopolymer according to one embodiment of the present invention is characterized in that it forms a complex with a lithium ion and a sodium ion among alkali metal ions, but does not form a complex with a potassium ion. Due to such characteristic of the azopolymer, the azopolymer is expected to be applied as the material of a sensor capable of selectively detecting specific alkali metal ions, or new material capable of selectively capturing specific alkali metal ions from a mixed solution of metal ions.

BRIEF DESCRIPTION OF DRAWINGS

FIG. 1 shows DSC heat curves for measuring the glass transition temperature, nematic liquid crystalline transition temperature and melting point of the azopolymers synthesized in Examples 1, 2 and 3.

FIG. 2 shows the $^1$H-NMR spectra of an azopolymer PDAEMA-S1 synthesized in Example 1, and azopolymer solutions into which alkali metal ions such as $Li^+$, $Na^+$, $K^+$ are introduced.

FIG. 3 shows the $^1$H-NMR spectra of an azopolymer PDAEMA-S2 synthesized in Example 2, and azopolymer solutions into which alkali metal ions such as $Li^+$, $Na^+$, $K^+$ are introduced.

FIG. 4 shows the $^1$H-NMR spectra of an azopolymer PDAEMA-S3 synthesized in Example 3, and azopolymer solutions into which alkali metal ions such as $Li^+$, $Na^+$, $K^+$ are introduced.

FIG. 5 shows the $^1$H-NMR spectra measured after irradiating UV of 365 nm wavelength for 5 minutes to an azopolymer PDAEMA-S1 synthesized in Example 1 and azopolymer solutions into which alkali metal ions such as $Li^+$, $Na^+$, $K^+$ are introduced.

FIG. 6 shows the $^1$H-NMR spectra measured after irradiating UV of 365 nm wavelength for 5 minutes to an azopolymer PDAEMA-S2 synthesized in Example 2 and azopolymer solutions into which alkali metal ions such as $Li^+$, $Na^+$, $K^+$ are introduced.

FIG. 7 shows the $^1$H-NMR spectra measured after irradiating UV of 365 nm wavelength for 5 minutes to an azopolymer PDAEMA-S3 synthesized in Example 3 and azopolymer solutions into which alkali metal ions such as $Li^+$, $Na^+$, $K^+$ are introduced.

DETAILED DESCRIPTION OF THE EMBODIMENTS

Hereinafter, an azomonomer with a novel structure and an azopolymer obtained by polymerization thereof, and a metal ions sensor and a capturing agent using the azopolymer, etc. according to specific embodiments of the present invention will be explained.

According to one embodiment of the present invention, an azomonomer represented by the following Chemical Formula 1 is provided.

[Chemical Formula 1]

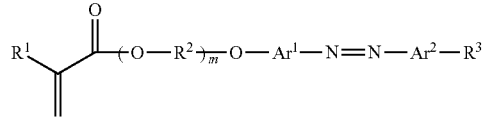

in the Chemical Formula 1, $R^1$ is hydrogen or a methyl group, $R^2$ is an alkylene group having 1 to 4 carbon atoms, $R^3$ is an alkyl group having 8 to 18 carbon atoms, each of $Ar^1$ and $Ar^2$ is independently an arylene group having 6 to 12 carbon atoms, and m is an integer of 1 to 5.

The azomonomer of the Chemical Formula 1 can provide an azopolymer that not only has excellent heat resistance but also can selectively capture and separate, or detect metal ions of a specific size. Such an effect is manifested from the specific structure of the azopolymer arising from the azomonomer.

In the azomonomer, the (meth)acryloyl group ($CH_2=CR^1-CO-$) is a polymerizable functional group and forms a main chain of azopolymer prepared from the azomonomer.

The alkyleneoxy group ($-O-R^2-$) linked to the (meth)acryloyl group may induce the azopolymer to selectively bond with a metal ion of a specific size. In such an alkyleneoxy group, $R^2$ may be, for example, methylene, 1,2-ethylene, 1,2-propylene, 1,3-propylene or 1,2-butylene, etc. For example, 1,2-ethylene may be adopted as R2 to provide the azopolymer capable of strongly bonding with a lithium ion.

The length of such an alkyleneoxy group may be easily controlled using an appropriate precursor as in Preparation Examples 2 to 4 described below. Referring to FIG. 1, as the length of the alkyleneoxy group increases, the glass transition temperature, nematic liquid crystalline transition temperature and melting point of the azopolymer tend to decrease. Thus, by controlling the length of the alkyleneoxy group of the Chemical Formula 1, heat resistance, etc. of the azopolymer may be easily controlled.

In the Chemical Formula 1, m may be an integer of 1 to 5, and when m is 2 or more, two or more $R^2$ may be all identical or at least one of two or more $R^2$ may be different. More appropriately, m may be an integer of 1 to 3 or an integer of 1. Referring to Experimental Examples described below, as the length of the alkyleneoxy group is shorter, the bonding force of the azopolymer with a specific metal ion may become stronger. Meanwhile, regardless of the length of the alkyleneoxy group (i.e., m in the Chemical Formula 1), the azopolymer may selectively bond with a metal ion of a specific size.

In the azomonomer, the azo group (—N═N—) reacts sensitively to light, thus enabling detection of an azopolymer bonded with a specific metal ion. For such a function, $Ar^1$ and $Ar^2$ linked to the azo group may be an arylene group having 6 to 12 carbon atoms, more appropriately a phenylene group.

And, the azomonomer, due to the alkyl chain having 8 to 18 carbon atoms introduced at the end ($R^3$), shows a tendency of gradual increase in a dispersion force or a van der waals force by the mutual interaction between the alkyl groups and the resulting aggregation of the molecules, i.e., a selfassembly behavior. Particularly, in case $R^3$ is an alkyl group having 10 to 16 carbon atoms, the selfassembly behavior may occur best.

Such a selfassembly behavior appears also in the azopolymer obtained from the azomonomers. Particularly, in the azopolymer, due to the selfassembly behavior, the side chains of the polymer may be regularly arranged. Thus, the movement of the alkyleneoxy group capable of capturing metal cations as well as the main chain or backbone of the azopolymer may be inhibited, thereby exhibiting the effect of immobilization of the polymer chain. The applicant expects that due to such an immobilization effect, the polymer provided from the azomonomers can easily capture metal ions even at a low concentration.

That is, the monomer of the Chemical Formula 1 has an alkyleneoxy group capable of capturing a metal cation of a specific size, and a long alkyl chain capable of providing a structure immobilized by a selfassembly behavior, thus providing polymer capable of detecting or capturing specific metal cations with high sensitivity.

In addition, the azomonomer of the Chemical Formula 1 has a structure partially similar to the monomers of liquid crystal polymers known as azopolymers, but exhibits totally different characteristics. The monomers capable of providing previously known liquid crystal polymers has a structure in which a polymerizable functional group exists at one end, and a functional group for causing electron density gradient in the molecule, and causing a difference in the structure of liquid crystal phase such as nematic, smectic or cholesteric or controlling the phase transition temperature (Tg, Tm or liquid crystal transition temperature) of the liquid crystal polymer exists at the other end. Specifically, the monomers capable of providing the existing liquid crystal polymers have a structure in which, at the $R^3$ position of the Chemical Formula 1, an electrodonating group such as a —$OCH_3$, —$NH_2$, or alkyl group (methyl, ethyl, butyl or chiral carbon-introduced alkyl group), or an electrowithdrawing group such as a —CN, —C(═O)H, —CO—, —COO— or —CONH— group is mainly introduced, instead of a long alkyl group. Particularly, since a primary alkyl group does not have a significant difference in the capability of donating electrons even if the carbon number increases, a long alkyl group has not been introduced at the $R^3$ position of the Chemical Formula 1, in the monomers for providing liquid crystal polymer.

Meanwhile, according to another embodiment of the present invention, an azopolymer comprising a repeat unit represented by the following Chemical Formula 2 is provided.

[Chemical Formula 2]

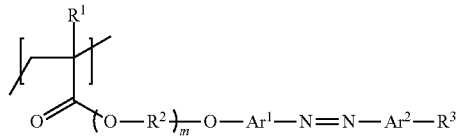

In the Chemical Formula 2, $R^1$, $R^2$, $R^3$, $Ar^1$, $Ar^2$ and m are as defined in the Chemical Formula 1.

The azopolymer can be obtained by polymerizing the above explained azomonomers of the Chemical Formula 1 by various methods known in the technical field to which the present invention pertains. As non-limiting examples, the azopolymer can be provided by radical polymerization of the azomonomers of the Chemical Formula 1 in the presence of a radical initiator.

Thus provided azopolymer has a structure in which a ligand group capable of bonding with specific metal ions, and an azo group having a light sensitivity and a long alkyl group exhibiting a selfassembly behavior are introduced at the side chain, as shown in the Chemical Formula 2.

The azopolymer can selectively capture metal ions of a specific size because it comprises a ligand group at the side chain unlike the existing ligands, and has very high sensitivity to light of a specific wavelength in the UV or visible light region because it comprises an azo group. And, if the azopolymer forms a complex with a specific metal ion, an NMR spectrum different from that of pure azopolymer is obtained. Thus, using the azopolymer, even a very low concentration of specific metal ions can be detected.

More specifically, the azo group of pure azopolymer may exist in thermodynamically stable trans structure and unstable cis structure. The trans structure and cis structure of the azo group exist at the ratio of about 95:5 at room temperature. If UV of about 360 nm wavelength is irradiated to the azopolymer comprising such an azo group, the trans structure is converted into the cis structure by photoisomerization of the azo group.

If such azopolymer forms a complex with a specific metal ion, the structure of the azopolymer is immobilized, and thus, even if UV is irradiated, photoisomerization of the azopolymer does not freely occur. Thus, referring to Experimental Example 2 described below, in case azopolymer forms a complex with a specific metal ion, change in absorption spectrum according to UV irradiation time is small compared to pure azopolymer, and as shown in FIG. 2 to FIG. 7, the azopolymer complex exhibits the same NMR results before and after UV irradiation.

And, if azopolymer forms a complex with a specific metal ion, as shown in Experimental Example 2 described below, red shift in which the maximum absorption wavelength by the cis structure of the azo group shifts to a longer wavelength occurs, and the absorption strength by the cis structure of the azo group rapidly increases.

And, if azopolymer forms a complex with a specific metal ion, an NMR spectrum different from that of pure azopolymer is obtained. More specifically, hydrogen atoms of the complex of azopolymer are more de-shielded than those of pure azopolymer, and thus, the hydrogen peaks of the azopolymer complex appear more downfield than those of pure azopolymer. And, referring to the Experimental Examples described below, the applicant found out that the unshared electron pair of the azo group and the alkyleneoxy group selectively bond with a metal ion of a specific size. Thus, the hydrogen peaks around the azo group of the azopolymer complex appear splitted unlike pure azopolymer, and the hydrogen peaks of the alkyleneoxy group of the azopolymer complex tend to be de-shielded unlike pure azopolymer.

Thus, through the absorption spectrum and/or NMR spectrum of azopolymer, the existence of a specific metal ion can be detected.

And, using the azopolymer, a specific metal ion can be separated from a mixture of metal ions. More specifically, the azopolymer is introduced into a mixture of metal ions to form a complex of the azopolymer with a specific metal ion, which is then mixed with a nonsolvent to precipitate the complex, thereby separating a specific metal ion in the mixture of metal ions.

For such a function, the azopolymer may be polymerized such that it may have a number average molecular weight of about 10,000 to 50,000 g/mol, and a molecular weight distribution of 1.2 to 4.0

And, the azopolymer may be homopolymer polymerized from the above explained azomonomers of the Chemical Formula 1. However, at a level that does not influence the above explained unique properties of the azopolymer, the azomonomers of the Chemical Formula 1 may be copolymerized with vinyl monomers that can be copolymerized such as styrene, methyl (meth)acrylate, acrylonitrile or vinyl chloride, to provide the azopolymer.

The above explained azopolymer may exhibit excellent thermal stability as well as the above explained characteristics. More specifically, the azopolymer has a glass transition temperature ($T_g$) of 60° C. to 120° C., nematic liquid crystalline transition temperature ($T_N$) of 90° C. to 160° C., and a melting point ($T_m$) of 110° C. to 210° C., thus exhibiting excellent heat resistance.

Meanwhile, according to still another embodiment of the present invention, metal ion sensor and metal ion capturing agent using the azopolymer are provided.

The azopolymer may selectively bond with a specific metal ion to form a complex, as explained above. And such a complex can be detected through UV-Vis absorption spectrum or NMR spectrum, and has excellent heat resistance, thus providing metal ion sensor and metal ion capturing agent that can be used under various environmental conditions.

For example, the azopolymer can selectively bond with a lithium ion and a sodium ion among alkali metal ions, and among them, strongly bond with a lithium ion to form a complex. Thus, using a metal ion sensor applying such azopolymer, it can be detected whether a lithium ion, a sodium ion or both exists in a mixture of various alkali metals, heavy metals, transition metals, etc. And, using a metal ion capturing agent applying such azopolymer, a lithium, ion, a sodium ion or both can be selectively separated from a mixture of various alkali metals, heavy metals, transition metals, etc.

Hereinafter, the action and the effects of the present invention will be explained through specific examples in more detail. However, these examples are presented only as the illustrations of the invention, and the scope of the invention is not limited thereby.

Preparation Example 1: Synthesis of 4-dodecyl-4'-hydroxyazobenzene (DHAB)

p-dodecylaniline (97%, 5.00 g, 18.60 mmol), HCl (4.85 mL, 55.00 mmol), NaNO$_2$ (1.32 g, 18.60 mmol), 156 mL of THF and 39 mL of distilled water were put in a 500 mL 3-neck round flask, and the solution was stirred at 0° C. under nitrogen atmosphere for 2 hours. Subsequently, into the flask, phenol (1.77 g, 18.60 mmol), K$_2$CO$_3$ (1.30 g, 19.10 mmol), Na$_2$CO$_3$ (1.44 g, 27.10 mmol), 128 mL of THF and 32 mL of H$_2$O were added, and the solution was additionally stirred at room temperature for 12 hours. Thereafter, the solvent was removed from the reaction solution using a rotary evaporator. Thus obtained solid was put in a separatory funnel containing 300 mL of methylenechloride (MC) and 300 mL of distilled water and strongly shaken, and then, an aqueous solution layer in which unreacted salts were dissolved was removed. Into the remaining MC solution, 10.0 g of anhydrous magnesium sulfate was introduced, and the solution was stirred for 30 minutes, and then, filtered to remove a trace amount of water dissolved in the organic layer. Thereafter, the solvent of the MC solution was evaporated, and the obtained solid was introduced into 300 mL of normal hexane and heated to 40° C. to dissolve, and then, cooled to recrystallize. The recrystallized solid product was filtered, and then, dried under reduced pressure for 24 hours in a vacuum oven to obtain yellow DHAB (yield: 65%; Tm: 90° C.).

The chemical structure of the synthesized DHAB was confirmed by hydrogen nuclear magnetic resonance ($^1$H-NMR) spectrum, and the result is as follows.

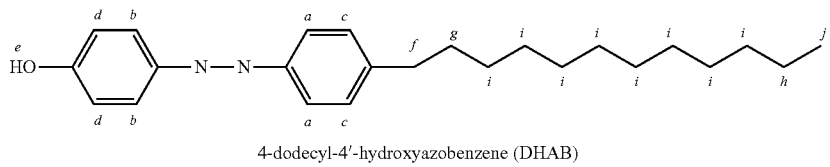 [SMILES: CCCCCCCCCCCCc1ccc(NNc2ccc(O)cc2)cc1]

4-dodecyl-4'-hydroxyazobenzene (DHAB)

$^1$H-NMR(CDCl$_3$, ppm): a, 7.86 (d, 2H); b, 7.79 (d, 2H); c, 7.30 (d, 2H); d, 6.94 (d, 2H); e, 5.04 (d, 1H); f, 2.67 (t, 2H); g, 1.65 (q, 2H); h, 1.32 (s, 2H); i, 1.26 (m, 16H); j, 0.88 (t, 3H).

Preparation Example 2: Synthesis of 2-(4-dodecylazobenzene-4'-oxy)ethanol (DAEA-S1)

DHAB synthesized in Preparation Example 1 (5.00 g, 13.60 mmol), K$_2$CO$_3$ (1.14 g, 8.25 mmol) and 50 mL of diglyme were put in a 2-neck round flask, and then, the solution was stirred at room temperature and nitrogen atmosphere for 30 minutes. Into the solution, 2-chloroethanol (2.20 g, 27.28 mmol) was introduced, and the solution was additionally stirred at 140° C. for 48 hours. The reaction solution was poured into 1 L of $H_2O$ to precipitate, and stirred for 1 hour to dissolve unreacted $K_2CO_3$, and then, filtered to obtain a solid precipitate containing unreacted DHAV and a product. The precipitate was dissolved in 200 mL of chloroform, 10.0 g of anhydrous magnesium sulfate was introduced therein, and the solution was stirred for 30 minutes and filtered to remove a trace amount of water dissolved in the precipitate. The solvent of the filtered chloroform solution was evaporated, and then, the obtained solid mixture was separated by column chromatography using a mixed solvent of normal hexane/ethyl acetate (EA)=1/1 (volume ratio) as a developing solvent, to obtain a yellow pure solid product 2-(4-dodecylazobenzene-4'-oxy) ethanol (DAEA-S1) (yield: 70%; Tm: 119° C.).

The chemical structure of the synthesized DAEA-S1 was confirmed by hydrogen nuclear magnetic resonance ($^1$H-NMR spectrum), and the result is as follows.

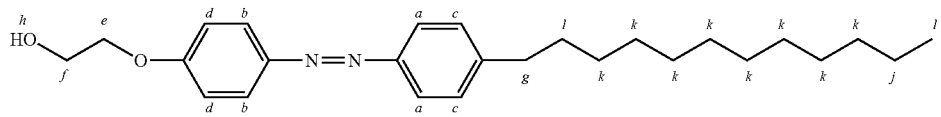

2-(4-dodecyl-azobenzene-4'-oxy)ethyl alcohol) (DAEA-S1)

$^1$H-NMR(CDCl$_3$, ppm): 7.90 (d, ArH, 2H), 7.80 (d, ArH, 2H), 7.30 (d, ArH, 2H), 7.04 (d, ArH, 2H), 4.17 (t, Ar-OCH$_2$, 2H), 4.01 (d, COOCH$_2$, 2H), 2.67 (t, Ar-CH$_2$, 2H), 2.07 (t, OH, H), 1.63 (q, ArCH$_2$CH$_2$, 2H), 1.32 (s, CH$_3$CH$_2$, 2H), 1.26 (m, —CH$_2$—, 16H), 0.88 (t, CH$_2$CH$_3$, 3H).

Preparation Example 3: Synthesis of 2-[2-(4-dodecylazobenzene-4'-oxy)ethoxy]ethanol (DAEA-S2)

A yellow pure solid product 2-[2-(4-dodecylazobenzene-4'-oxy)ethoxy]ethyl alcohol (DAEA-S2) was obtained (yield: 87%; Tm: 106° C.) by the same method as Preparation Example 2, except that 2-(2-chloroethoxy)ethanol (3.40 g, 27.28 mmol) was introduced instead of 2-chloroethanol in Preparation Example 2.

The chemical structure of the synthesized DAEA-S2 was confirmed by $^1$H-NMR spectrum, and the result is as follows.

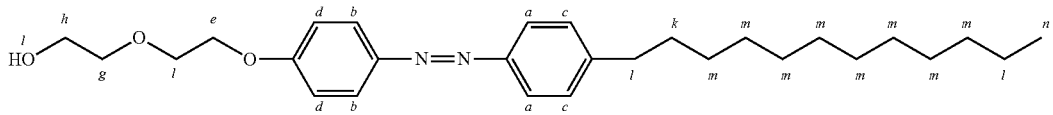

2-[2-(4-dodecyl-azobenzene-4'-oxy)ethyl-oxy]ethyl alcohol) (DAEA-S2)

$^1$H-NMR(CDCl$_3$, ppm): 7.90 (d, ArH, 2H), 7.80 (d, ArH, 2H), 7.30 (d, ArH, 2H), 7.03 (d, ArH, 2H), 4.23 (t, Ar-OCH$_2$, 2H), 3.92 (t, COOCH$_2$, 2H), 3.79 and 3.70 (t, CH$_2$OCH$_2$, 4H), 2.67 (t, Ar-CH$_2$, 2H), 2.07 (t, OH, H), 1.63 (q, ArCH$_2$CH$_2$, 2H), 1.32 (s, CH$_3$CH$_2$, 2H), 1.26 (m, —CH$_2$—, 16H), 0.88 (t, CH$_2$CH$_3$, 3H).

Preparation Example 4: Synthesis of 2-{2-[2-(4-dodecylazobenzene-4'-oxy(ethoxy]ethoxy}ethanol (DAEA-S3)

A yellow pure solid product 2-{2-[2-(4-dodcylazobenzene-4'-oxy)ethoxy]ethoxy}ethyl alcohol (DAEA-S3) was obtained (yield: 71%; T$_m$: 92° C.) by the same method as Preparation Example 2, except that 2-[2-(2-chloroethoxy)ethoxy]ethanol (4.60 g, 27.28 mmol) was introduced instead of 2-chloroethanol in Preparation Example 2.

The chemical structure of the synthesized DAEA-S3 was confirmed by $^1$H-NMR spectrum, and the result is as follows.

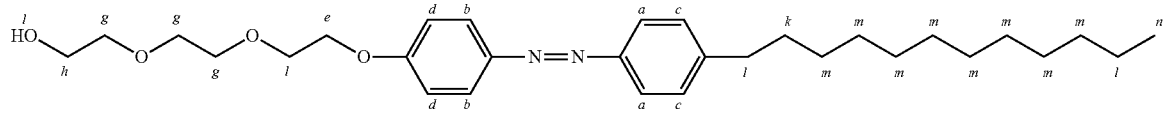

2-{2-[2-(4-dodecyl-azobenzene-4'-oxy)ethyl-oxy]ethyl-oxy}ethyl alcohol) (DAEA-S3)

$^1$H-NMR(CDCl$_3$, ppm): 7.89 (d, ArH, 2H), 7.79 (d, ArH, 2H), 7.30 (d, ArH, 2H), 7.03 (d, ArH, 2H), 4.23 (t, Ar-OCH$_2$, 2H), 3.91 (t, COOCH$_2$, 2H), 3.73 and 3.63 (t, CH$_2$OCH$_2$, 8H), 2.67 (t, Ar-CH$_2$, 2H), 2.31 (s, OH, H), 1.63 (q, ArCH$_2$CH$_2$, 2H), 1.32 (s, CH$_3$CH$_2$, 2H), 1.26 (m, —CH$_2$—, 16H), 0.88 (t, CH$_2$CH$_3$, 3H).

Preparation Example 5: Preparation of azomonomer [2-(4-dodecylazobenzene-4'-oxy)ethyl methacrylate (DAEMA-S1)]

DAEA-S1 (2.00 g, 4.87 mmol) prepared in Preparation Example 2, triethylamine (0.59 g, 5.85 mmol) and 100 mL of anhydrous THF 100 mL were put in a 1-neck round flask, and the solution was stirred at room temperature and nitrogen atmosphere for 30 minutes. Subsequently, into the flask, methacryloyl chloride (0.61 g, 5.85 mmol) was introduced, and the solution was additionally stirred at room temperature for 24 hours. Thereafter, the solvent was removed from the reaction solution using an evaporator. Thus obtained solid was put in a separatory funnel together with 300 mL of NaHCO$_3$ aqueous solution (5 wt % in H$_2$O), and then, the aqueous solution layer was separated to remove unreacted methacryloyl chloride. Into the separated MC solution, 1.0 g of anhydrous magnesium sulfate was introduced, and the solution was stirred for 30 minutes and then filtered to remove a trace amount of water. The solvent of the filtered chloroform solution was evaporated, and then, separated by column chromatography using a mixed solution of normal hexane/EA=3:1 (volume ratio) to obtain a yellow solid product, 2-(4-dodecylazobenzene-4'-oxy)ethyl methacrylate (DAEMA-S1) monomers (yield: 73%; T$_m$: 61° C.).

The chemical structure of the synthesized DAEMA-S1 was confirmed by $^1$H-NMR spectrum, and the result is as follows.

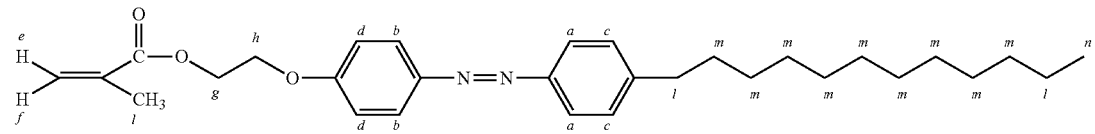

2-(4-dodecyl-azobenzene-4'-oxy)ethyl methacrylate (DAEMA-S1)

$^1$H-NMR(CDCl$_3$, ppm): 7.90 (d, ArH, 2H), 7.80 (d, ArH, 2H), 7.30 (d, ArH, 2H), 7.03 (d, ArH, 2H), 6.17 and 5.61 (s, =CH$_2$, 2H), 4.53 (t, Ar-OCH$_2$, 2H), 4.31 (t, COOCH$_2$, 2H), 2.67 (t, Ar-CH$_2$, 2H), 1.97 (s, CCH$_3$, 3H), 1.65 (q, ArCH$_2$CH$_2$, 2H), 1.32 (s, CH$_3$CH$_2$, 2H), 1.26 (m, —CH$_2$-, 16H), 0.88 (t, CH$_2$CH$_3$, 3H).

Preparation Example 6: Preparation of azomonomer [2-[2-(4-dodecylazobenzene-4'-oxy)ethoxy]ethyl methacrylate (DAEMA-S2)]

Yellow 2-[2-(4-dodecylazobenzene-4'-oxy)ethyleneoxy]ethyl methacrylate (DAEMA-S2) monomers were obtained by the same method as Preparation Example 5, except using DAEA-S2 (2.00 g, 4.40 mmol) of Preparation Example 3 in Preparation Example 5 (yield: 28%; T$_m$: 53° C.).

The chemical structure of the synthesized DAEMA-S2 was confirmed by $^1$H-NMR spectrum, and the result is as follows.

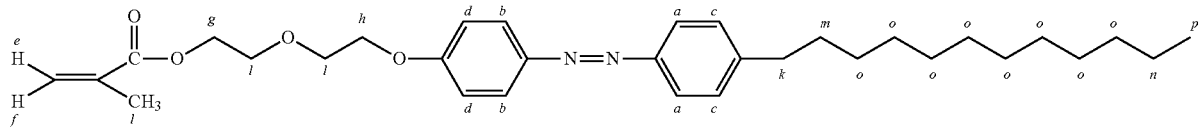

2-[2-(4-dodecyl-azobenzene-4'-oxy)ethylene-oxy]ethyl methacrylate (DAEMA-S2)

$^1$H-NMR(CDCl$_3$, ppm): 7.89 (d, ArH, 2H), 7.80 (d, ArH, 2H), 7.30 (d, ArH, 2H), 7.02 (d, ArH, 2H), 6.13 and 5.58 (s, =CH$_2$, 2H), 4.35 (t, Ar-OCH$_2$, 2H), 4.22 (t, COOCH$_2$, 2H), 3.91 and 3.85 (t, CH$_2$OCH$_2$, 4H), 2.67 (t, Ar-CH$_2$, 2H), 1.95 (s, CCH$_3$, 3H), 1.65 (q, ArCH$_2$CH$_2$, 2H), 1.32 (s, CH$_3$CH$_2$, 2H), 1.26 (m, —CH$_2$—, 16H), 0.88 (t, CH$_2$CH$_3$, 3H).

Preparation Example 7: Preparation of azomonomer [2-{2-[2-(4-dodecylazobenzene-4'-oxy)ethoxy]ethoxy}-ethyl methacrylate (DAEMA-S3)]

Yellow 2-{2-[2-(4-dodecylazobenzene-4'-oxy)ethyleneoxy]ethyloxy}ethyl methacrylate (DAEMA-S3) were obtained by the same method as Preparation Example 5, except using DAEA-S3 (2.00 g, 4.01 mmol) of Preparation Example 4 in Preparation Example 5 (yield: 73%; T$_m$: 50° C.).

The chemical structure of the synthesized DAEMA-S3 monomer was confirmed by $^1$H-NMR spectrum, and the result is as follows.

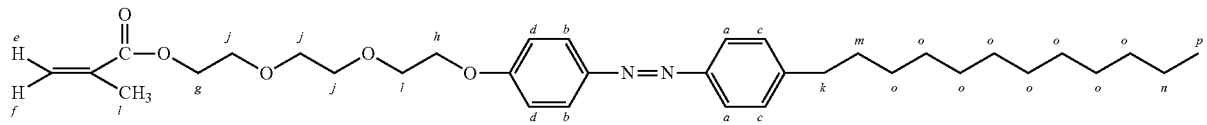

2-{2-[2-(4-dodecyl-azobenzene-4'-oxy)ethylene-oxy]ethyl-oxy}ethyl methacrylate (DAEMA-S3)

$^1$H-NMR(CDCl$_3$, ppm): 7.89 (d, ArH, 2H), 7.80 (d, ArH, 2H), 7.30 (d, ArH, 2H), 7.02 (d, ArH, 2H), 6.14 and 5.57 (s, =CH$_2$, 2H), 4.32 (t, Ar-OCH$_2$, 2H), 4.21 (t, COOCH$_2$, 2H), 3.90 and 3.74 (t, CH$_2$OCH$_2$, 8H), 2.67 (t, Ar-CH$_2$, 2H), 1.95 (s, CCH$_3$, 3H), 1.65 (q, ArCH$_2$CH$_2$, 2H), 1.32 (s, CH$_3$CH$_2$, 2H), 1.26 (m, —CH$_2$—, 16H), 0.88 (t, CH$_2$CH$_3$, 3H).

Example 1: Preparation of Azopolymer (PDAEMA-S1)

DAEMA-S1 (0.50 g, 1.04 mmol) of Preparation Example 5, Anisole (2.25 mL) and a radical initiator (Azoisobutyronitrile, AIBN 5.00 mg) were put into a 15 mL ampule, oxygen existing in the solution was removed by a freeze-thawing method, and then, the ampule was sealed, and a radical polymerization reaction was progressed at 70° C. for 48 hours. After completing the polymerization reaction, THF (5 mL) was introduced into the polymer solution to dilute, and then, the polymer solution was poured into 300 mL of methanol to precipitate. The obtained mixture was filtered and dried to obtain polymer. The prepared polymer was dissolved in a THF solvent again and reprecipitated in an excessive amount of methanol, and the solution was filtered, and then, dried in a vacuum oven of room temperature for 24 hours to obtain azopolymer PDAEMA-S1. Polymer conversion rate was 64%, and the number average molecular weight (M$_n$) was 37,600 g/mol. The molecular weight distribution of the polymer was 3.26, and the melting point (T$_m$) was 192 to 194° C.

The chemical structure of the azopolymer PDAEMA-S1 was confirmed by $^1$H-NMR spectrum, and the result is as follows.

$^1$H-NMR(CDCl$_3$, ppm): 7.72 (m, ArH, 4H), 7.18 (m, ArH, 2H), 6.77 (m, ArH, 2H), 4.12 (m, OCH$_2$CH$_2$, 4H), 2.57 (m, Ar-CH$_2$, 2H), 1.85 (m, CCH$_2$, 3H), 1.57 (m, ArCH$_2$CH$_2$, 2H), 1.23 (m, —CH$_2$—, 18H), 1.05 (m, —CH$_2$—, 3H), 0.86 (m, CH$_2$CH$_3$, 3H).

Example 2: Preparation of Azopolymer (PDAEMA-S2)

Azopolymer PDAEMA-S2 was obtained by the same method as Example 1, except that DAEMA-S2 (0.50 g, 0.96 mmol) of Preparation Example 6 and THF (2.25 mL) were used instead of DAEMA-S1 (0.50 g, 1.04 mmol) of Preparation Example 5 and Anisole (2.25 mL) in Example 1. Polymer conversion rate was 58%, and the number average molecular weight (M$_n$) was 27,400 g/mol. The molecular weight distribution of the polymer was 2.10, and the melting point (T$_m$) was 157 to 159° C.

The chemical structure of the azopolymer PDAEMA-S2 was confirmed by $^1$H-NMR spectrum, and the result is as follows.

$^1$H-NMR(CDCl$_3$, ppm): 7.79 (d, ArH, 2H), 7.72 (d, ArH, 2H), 7.19 (d, ArH, 2H), 6.91 (m, ArH, 2H), 4.04 (m, Ar—OCH$_2$, COOCH$_2$, 4H), 3.69 and 3.62 (m, CH$_2$OCH$_2$, 2H), 2.58 (m, Ar-CH$_2$, 2H), 1.88 (m, CCH$_2$, 3H), 1.58 (m, ArCH$_2$CH$_2$, 2H), 1.22 (m, —CH$_2$—, 18H), 1.07 (m, —CH$_2$—, 3H), 0.85 (m, CH$_2$CH$_3$, 3H).

Example 3: Preparation of Azopolymer (PDAEMA-S3)

Azopolymer PDAEMA-S3 was obtained by the same method as Example 1, except that DAEMA-S3 (0.50 g, 0.88 mmol) of Preparation Example 7 and an initiator BPO (5.00 mg) were used instead of DAEMA-S1 (0.50 g, 1.04 mmol) of Preparation Example 5 and Anisole (2.25 mL) in Example 1. Polymer conversion rate was 32%, and the number average molecular weight (M$_n$) was 33,500 g/mol. The molecular weight distribution of the polymer was 1.78, and the melting point (T$_m$) was 132° C.

The chemical structure of the azopolymer PDAEMA-S3 was confirmed by $^1$H—NMR spectrum, and the result is as follows.

$^1$H-NMR(CDCl$_3$, ppm): 7.81 (d, ArH, 2H), 7.74 (d, ArH, 2H), 7.22 (d, ArH, 2H), 6.93 (d, ArH, 2H), 4.08 (m, Ar—OCH$_2$, COOCH$_2$, 4H), 3.79, 3.64 and 3.60 (m, CH$_2$OCH$_2$, 8H), 2.59 (m, Ar-CH$_2$, 2H), 1.88 (m, CCH$_2$, 3H), 1.58 (m, ArCH$_2$CH$_2$, 2H), 1.23 (m, —CH$_2$—, 18H), 1.07 (m, —CH$_2$—, 3H), 0.85 (m, CH$_2$CH$_3$, 3H).

Experimental Example 1: Property Evaluation of Azopolymer

The glass transition temperature (Tg), nematic liquid crystalline transition temperature (T$_N$) and melting temperature (T$_m$) of the azopolymers synthesized in Examples 1, 2 and 3 were measured with a differential scanning calorimeter (DSC), and the results are shown in FIG. 1.

Referring to FIG. 1, the azopolymers synthesized in Examples 1 to 3 exhibit stable phase transition, thus confirming selfassembly behavior by the alkyl chain introduced at the end, and it is confirmed that as the length of the ethyleneoxy group in the azopolymer increases, the glass transition temperature, nematic liquid crystalline transition temperature and melting temperature of the azopolymer tend to decrease.

Experimental Example 2: Optical Property Evaluation of Azopolymer Complex

<Preparation of a Complex of Azopolymer>

The azopolymers synthesized in Examples 1 to 3 and the metal salts of $LiPF_6$, $NaPF_6$ and $KPF_6$ were introduced into 100 mL of a mixed solvent of chloroform/acetonitrile=3/1 volume ratio at the contents described in the following Table 1, and the solution was stirred for 1 hour, thereby inducing the azopolymers to form complexes with $Li^+$, $Na^+$ or $K^+$ cations released from the metal salt.

TABLE 1

|  | PDAEMA-S1 | PDAEMA-S2 | PDAEMA-S3 | $LiPF_6$ | $NaPF_6$ | $KPF_6$ |
|---|---|---|---|---|---|---|
| complex 1 | 2.3 mg |  |  | 100 equivalents |  |  |
| complex 2 | 2.3 mg |  |  |  | 100 equivalents |  |
| complex 3 | 2.3 mg |  |  |  |  | 100 equivalents |
| complex 4 |  | 2.6 mg |  | 100 equivalents |  |  |
| complex 5 |  | 2.6 mg |  |  | 100 equivalents |  |
| complex 6 |  | 2.6 mg |  |  |  | 100 equivalents |
| complex 7 |  |  | 2.8 mg | 100 equivalents |  |  |
| complex 8 |  |  | 2.8 mg |  | 100 equivalents |  |
| complex 9 |  |  | 2.8 mg |  |  | 100 equivalents |

In the Table 1, the content unit of $LiPF_6$, $NaPF_6$ and $KPF_6$ is 'equivalent', which means the 'equivalent' of the metal salts per 1 equivalent of the polymer.

In the case of complex 1, complex 2, complex 4, complex 5, complex 7 and complex 8, after adding the metal salts, the color of the complexes changed from light yellow to dark orange. And, in the complex 1, complex 4 and complex 7 obtained by adding $LiPF_6$ salts, darker colors were manifested compared to the complex 2, complex 5 and complex 8 obtained by adding $NaPF_6$ salts.

However, in the complex 3, complex 6 and complex 9 obtained by adding $KPF_6$ salts to the azopolymer solutions synthesized in Examples 1 to 3, the colors of the solutions did not change.

Thus, it is confirmed that the azopolymers synthesized in Examples 1 to 2 can form a complex with $Li^+$ and $Na^+$ cations, and cannot form a complex with a $K^+$ cation, and the azopolymers synthesized in Examples 1 to 3 have higher selectivity to $Li^+$ cation than $Na^+$ cation.

Such results are also confirmed through the following optical property evaluation and NMR evaluation.

In general, an azobenzene group comprises a thermodynamically stable trans structure and unstable cis structure at a ratio of about 95:5 at room temperature. Thus, in the absorption spectrum of a solution comprising a unimolecule or polymer into which an azobenzene group is introduced, a strong absorption band appears due to the stable trans structure around about 360 nm, and a weak absorption band appears due to the unstable cis structure around about 450 nm. If UV of about 360 nm wavelength is irradiated to the solution, the trans structure is converted into the cis structure by the photoisomerization reaction of the azobenzene group. Here, the speed of the structure conversion is proportional to the intensity and irradiation time of W. However, the unstable cis structure spontaneously returns to the trans structure if external stimulus disappears.

Based on this principle, the applicability of the azopolymer according to one embodiment of the present invention as an alkali metal ion sensor was examined. For this, the absorption spectra of the complexes 1 to 9 were measured using a UV-Vis spectrophotometer, and UV of 365 nm wavelength was irradiated to the complexes 1 to 9 for 5 minutes and then the absorption spectra were measured by the same method.

And, in order to compare with the measurement results of the absorption spectra of the complexes, solutions of the azopolymers synthesized in Examples 1 to 3 were prepared, and the absorption spectra were measured respectively before and after irradiating UV of 365 nm wavelength to the pure azopolymer solutions by the same method as explained above.

Meanwhile, the absorbance ((A), no unit) of the UV-Vis spectrum of the solution at a given wavelength is proportional to the molar absorptivity (($\varepsilon$), $L*mol^{-1}*cm^{-1}$) of the sample dissolved in the solvent, the concentration (c, mol/L) of the sample and the distance (b, cm) of the solution through which light passes, respectively, and is defined as the Equation: $A=\varepsilon bc$.

Thus, the ratio of the trans and cis structures of the azo group existing in the complex or pure azopolymer solution can be calculated from the relative ratio (%) of the absorbance at the maximum absorption wavelength, i.e., the following Equation.

$$\text{The ratio of trans or cis structures}(\%)=[(A_{trans} \text{ or } A_{cis})/(A_{trans}+A_{cis})]\times 100$$

In the following Table 2, wavelength at which a strong absorption band appears due to the trans structure before and after UV irradiation, absorbance at the wavelength and the ratio of the trans structure calculated from the absorbance, and wavelength at which a strong absorption band appears due to the cis structure before and after UV irradiation, absorbance at the wavelength and the ratio of cis structure calculated from the absorbance, in the absorption spectra obtained using the azopolymer solutions synthesized in Examples 1 to 3, are shown.

TABLE 2

|  |  |  | Example 1 | Example 2 | Example 3 |
|---|---|---|---|---|---|
| Trans structure | Before UV irradiation | Wavelength | 347 nm | 350 nm | 351 nm |
|  |  | Absorbance | 1.13 | 0.89 | 1.33 |
|  |  | Ratio | 97% | 93% | 95% |
|  | 5 minutes after UV irradiation | Wavelength | 347 nm | 350 nm | 351 nm |
|  |  | Absorbance | 0.05 | 0.06 | 0.05 |
|  |  | Ratio | 34% | 38% | 30% |
| Cis structure | Before UV irradiation | Wavelength | 443 nm | 445 nm | 442 nm |
|  |  | Absorbance | 0.03 | 0.06 | 0.07 |
|  |  | Ratio | 3% | 7% | 5% |
|  | 5 minutes after UV irradiation | Wavelength | 445 nm | 445 nm | 444 nm |
|  |  | absorbance | 0.09 | 0.10 | 0.12 |
|  |  | Ratio | 66% | 62% | 70% |

Referring to the Table 2, in the case of the azopolymers synthesized in Examples 1 to 3, irrespective of the length of an ethyleneoxy group, a strong absorption band and a weak absorption band due to the trans and cis structures of the azobenzene group appear respectively at a wavelength of about 350 nm and 445 nm.

If UV is irradiated to the azopolymer solutions, the trans structure of the azobenzene is converted into the cis structure through the photoisomerizatoin reaction of the azobenzene in proportion to the UV irradiation time. Thus, it is confirmed that, in proportion to the UV irradiation time, the intensity of the absorption band due to the trans structure appearing at about 350 nm decreases, and the intensity of the absorption band due to the cis structure appearing at about 445 nm increases very gradually.

In the following Table 3, wavelength at which a strong absorption band appears due to the trans structure before and after UV irradiation, absorbance at the wavelength and the ratio of the trans structure calculated from the absorbance, and wavelength at which a strong absorption band appears due to the cis structure before and after UV irradiation, absorbance at the wavelength and the ratio of cis structure calculated from the absorbance, in the absorption spectra obtained using the complexes prepared by adding LiPF$_6$ to the azopolymer solutions synthesized in Examples 1 to 3, are shown.

TABLE 3

|  |  |  | complex 1 | complex 4 | complex 7 |
|---|---|---|---|---|---|
| Trans structure | Before UV irradiation | Wavelength | 347 nm | 351 nm | 352 nm |
|  |  | absorbance | 1.01 | 1.08 | 1.15 |
|  |  | Ratio | 76% | 76% | 75% |
|  | 5 minutes after UV irradiation | Wavelength | 347 nm | 351 nm | 352 nm |
|  |  | absorbance | 0.83 | 0.86 | 0.95 |
|  |  | Ratio | 69% | 69% | 69% |
| Cis structure | Before UV irradiation | Wavelength | 470 nm | 469 nm | 471 nm |
|  |  | Absorbance | 0.31 | 0.34 | 0.38 |
|  |  | Ratio | 24% | 24% | 25% |
|  | 5 minutes after UV irradiation | Wavelength | 468 nm | 468 nm | 468 nm |
|  |  | Absorbance | 0.37 | 0.40 | 0.42 |
|  |  | Ratio | 31% | 31% | 31% |

Referring to the result of Example 1 in the Table 2, in the case of the solution of pure azopolymer PDAEMA-S1, the relative ratio (ratio for the intensity of the maximum absorption wavelength) of the cis structure to the trans structure before UV irradiation, as calculated by the above explained method, was 3%. However, referring to the result of the complex 1 in the Table 3, in the case of the solution of azopolymer PDAEMA-S1 in to which LiPF$_6$ metal salt is introduced, the relative ratio (ratio for the intensity of the maximum absorption wavelength) of the cis structure to the trans structure before UV irradiation was 24%. Thus, it is confirmed that if azopolymer forms a complex with a Li$^+$ cation, not only the relative ratio of the cis structure to the trans structure of the azobenzene group rapidly increases, but also the width of the absorption band broadens from about 100 nm to 150 nm.

And, referring to the result of the complex 1 in the Table 3, compared to pure azopolymer, there is no change in the maximum absorption wavelength ($\lambda_{max}$) for the trans structure in the complex 1, but red shift occurred wherein the maximum absorption wavelength for the cis structure shifts to about 23 nm to 27 nm longer wavelength, i.e., from 442 nm to 445 nm, to 468 nm to 470 nm. And, in case UV was irradiated up to 5 minutes after the complex was formed, the ratio of the cis structure displayed a tendency to increase from 24% before irradiation to the maximum 31%.

And, comparing the result of Example 1 in the Table 2 and the result of the complex 1 in the Table 3, in the absorption spectrum of the complex 1, compared to the absorbance before UV irradiation of the azopolymer solution into which a metal salt is not introduced, the absorbance of the trans structure before and after UV irradiation decreases by about 21 to 28%, while the absorbance of the cis structure rapidly increases by about 8 to 10.3 times.

Such a result also corresponds to the experimental result of the solutions (complexes 4 and 7) of the azopolymers (PDAEMA-S2 and PDAEMA-S3) with increased ethyleneoxy group lengths. Specifically, referring to the complexes 4 and 7 of the Table 3, when the azopolymers (PDAEMA-S2 and PDAEMA-S3) formed complexes with Li$^+$ cations, the maximum absorption wavelength of the cis structure before and after UV irradiation shifted to minimum 23 nm and maximum 29 nm longer wavelength. And, from the result of rapid increase in the absorbance by minimum 3.4 times to maximum 6.2 times, it can be considered that the molar absorptivity value of the cis structure significantly increases.

In the following Table 4, wavelength at which a strong absorption band appears due to the trans structure before and after UV irradiation, absorbance at the wavelength and the ratio of the trans structure calculated from the absorbance, and wavelength at which a strong absorption band appears due to the cis structure before and after UV irradiation, absorbance at the wavelength and the ratio of cis structure calculated from the absorbance, in the absorption spectra obtained using the complexes prepared by adding NaPF$_6$ to the azopolymer solutions synthesized in Examples 1 to 3, are shown.

[표 4]

|  |  |  | complex 2 | complex 5 | complex 8 |
|---|---|---|---|---|---|
| Trans structure | Before irradiation | Wavelength | 348 nm | 351 nm | 351 nm |
|  |  | Absorbance | 1.14 | 1.28 | 1.31 |
|  |  | Ratio | 94% | 92% | 92% |
|  | 5 minutes after irradiation | Wavelength | 348 nm | 351 nm | 351 nm |
|  |  | Absorbance | 0.91 | 0.80 | 0.99 |
|  |  | Ratio | 87% | 85% | 84% |
| Cis structure | Before irradiation | Wavelength | 444 nm | 442 nm | 439 nm |
|  |  | Absorbance | 0.07 | 0.12 | 0.11 |
|  |  | Ratio | 6% | 8% | 8% |
|  | 5 minutes after irradiation | Wavelength | 445 nm | 443 nm | 441 nm |
|  |  | Absorbance | 0.14 | 0.14 | 0.19 |
|  |  | Ratio | 13% | 15% | 16% |

Referring to the Table 4, in the case of the complex solutions of azopolymers into which NaPF$_6$ metal salt is introduced, compared to the solution of azopolyemr itself, change in the maximum absorption wavelength by the trans structure of azobenzene was hardly observed. However, in the case of the complex solutions of azopolymers into which NaPF$_6$ metal salt is introduced, before and after UV irradiation, only the absorbance of the trans structure of azobenzene decreased a little, compared to the values of the solutions of azopolymer itself before UV irradiation, by maximum 10% (PDAEMA-S1), 8% (PDAEMA-S2) and 11% (PDAEMA-S3), unlike the above explained complex solution with Li$^+$. Besides, there is little change in the maximum absorption wavelength of the cis structure of the complex before and after UV irradiation, and the absorbance increased by about 2 times.

In the following Table 5, wavelength at which a strong absorption band appears due to the trans structure before and after UV irradiation, absorbance at the wavelength and the ratio of the trans structure calculated from the absorbance, and wavelength at which a strong absorption band appears due to the cis structure before and after UV irradiation, absorbance at the wavelength and the ratio of cis structure calculated from the absorbance, in the absorption spectra obtained using the complexes prepared by adding KPF$_6$ to the azopolymer solutions synthesized in Examples 1 to 3, are shown.

TABLE 5

| | | | complex 3 | complex 6 | complex 9 |
|---|---|---|---|---|---|
| Trans structure | Before irradiation | Wavelength | 349 nm | 349 nm | 352 nm |
| | | Absorbance | 0.98 | 1.06 | 1.11 |
| | | Ratio | 93% | 93% | 92% |
| | 5 minutes after irradiation | Wavelength | 349 nm | 349 nm | 352 nm |
| | | Absorbance | 0.09 | 0.09 | 0.08 |
| | | Ratio | 43% | 41% | 35% |
| Cis structure | Before irradiation | Wavelength | 443 nm | 443 nm | 443 nm |
| | | Absorbance | 0.07 | 0.08 | 0.09 |
| | | Ratio | 7% | 7% | 8% |
| | 5 minutes after irradiation | Wavelength | 443 nm | 444 nm | 445 nm |
| | | Absorbance | 0.11 | 0.13 | 0.14 |
| | | ratio | 57% | 59% | 65% |

Referring to the Table 5, in the case of the solutions of azopolymers into which KPF$_6$ metal salt is introduced, unlike to the absorption spectra of the solutions of azopolymer complex into which Li$^+$ or Na$^+$ cation is introduced, as the UV irradiation time increases, the intensity of the absorption of the stable trans structure of azobenzene rapidly decreases and the trans structure is converted into cis structure maximum 65%, and any change in the maximum absorption wavelength of the cis structure was not observed at all. As the result, the absorption spectra of the solutions of azopolymers into which KPF$_6$ metal salt is introduced almost correspond to the absorption spectra of the solutions of azopolymer itself. From this result, it is confirmed that the azopolymer according to one embodiment of the present invention cannot form a complex with K$^+$ cation, regardless of the length of the ethyleneoxy group introduced therein.

Based on the above results, it can be expected that at least a part of the metal ions bonded with azopolymer bond with the cis-azo group of the azopolymer to form a complex by the following mechanism.

That is, the azo group existing in azopolymer exist in thermodynamically stable trans structure and unstable cis structure at a ratio of 95%: 5% at room temperature (error range ±2%). Here, if Li$^+$ cation released from a LiPF$_6$ metal salt exists, it strongly bond with the unshared electron pair of the nitrogen atom making up the cis structure, to form a new complex structure. However, if Na$^+$ cation released from a NaPF$_6$ metal salt exists, a complex having a weaker bonding force than the complex derived from Li$^+$ cation is formed. The reason is that not only the radius of the cation is much smaller, but also Li$^+$ cation with high electron affinity forms a cis complex having much stronger bonding force than Na$^+$. As the result, if Li$^+$ cation exists, the maximum absorption wavelength derived from the cis structure shifted to 20 nm or more longer wavelength before and after UV irradiation, compared to the solution of azopolymer itself without metal salt, the value of molar absorptivity of the complex significantly increased and the absorbance also increased rapidly. However, in the case of a complex solution derived from Na$^+$, the trans structure decreased by just 7% before and after UV irradiation, the cis structure only increased by about 2 times, and the maximum absorption wavelength and the absorbance were almost identical to those of the solution of azopolymer itself without metal salt. Meanwhile, in the case of K$^+$ cation, a complex was not formed.

From these results, it was found out that the azopolymer according to one embodiment of the present invention exhibits most excellent selectivity to Li$^+$ cation among alkali metal cations. And, it was also confirmed that the length of introduced ethyleneoxy group is unrelated to the selectivity to cation. In conclusion, it could be confirmed that the selectivity according to the size of alkali metal cations is Li$^+$>>Na$^+$>>K$^+$ (no selectivity) in order, regardless of the length of the ethyleneoxy group introduced in the azopolymer.

Experimental Example 4: NMR Evaluation of Azopolymer Complex

The azopolymers (PDAEMA-S1, PDAEMA-S2 or PDAEMA-S3, 7.5×10$^{-3}$ M) synthesized in Examples 1 to 3 and alkali metal salts LiPF$_6$, NaPF$_6$ or KPF$_6$ (100 equivalents per 1 equivalent of the polymer) were introduced into a mixed solvent of CDCl$_3$ (0.60 mL) and CD$_3$CN (0.20 mL), and the solution was stirred for 10 minutes to prepare solutions into which metal salts are introduced. Thereafter, $^1$H-NMR (400 MHz) spectrum of each solution was measured at room temperature, and shown in FIGS. 2 to 4.

Referring to FIG. 2a, in the NMR spectrum of pure azopolymer(PDAEMA-S1), hydrogen peaks of trans-azobenzene group mainly existing at room temperature (about 95±2%) are confirmed. Specifically, in the pure azopolymer (PDAEMA-S1), among the 8 hydrogen atoms existing in the trans-azobenzene group, 4 hydrogen atoms existing at the ortho position of the azo group —N═N— appear as singlet peak at 7.68 ppm (1$^{st}$ and 2$^{nd}$ hydrogen, 4H), and 4 hydrogen atoms existing at the meta position of

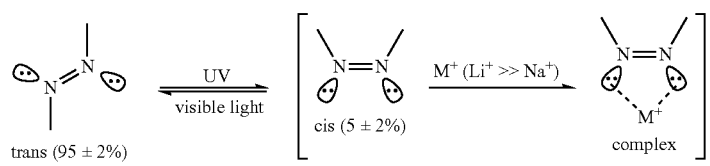

the azo group —N=N— appear as two singlet peaks at 7.15 ppm ($3^{rd}$ hydrogen, 2H) and 6.76 ppm ($4^{th}$ hydrogen, 2H).

However, referring to FIG. 2b and FIG. 2c, in case $Li^+$ or $Na^+$ cation released from a $LiPF_6$ or $NaPF_6$ metal salt forms a complex with PDAEMA-S1, unlike the above result, among 8 hydrogen atoms existing in azobenzene (trans-azobenzene content: 94-75%, cis-azobenzene content: 6-25%), 4 hydrogen atoms existing at the ortho position of the azo group appear splitted as two singlet peaks at about 8.0 ppm ($1^{st}$ hydrogen, 2H) and 7.8 ppm ($2^{nd}$ hydrogen, 2H). And, hydrogen atoms existing at the meta position of the azo group also appear as two singlet peaks at 7.3 ppm ($3_{rd}$ hydrogen of FIGS. 2b and 2c, 2H), 7.1 ppm ($4^{th}$ hydrogen of FIGS. 2b and 2c, 2H). And, in the complex of azopolymer, compared to the pure azopolymer, the positions of hydrogen peaks of trans-azobenzene all shift downfield by 0.2 to 0.4 ppm. And, in the case of the complexes, the positions of hydrogen peaks of ethyleneoxy [—$CH_2CH_2O$—] group introduced as a ligand capable of bonding with a metal cation ($5^{th}$ hydrogen of FIGS. 2b and 2c, 4H, 4.43 ppm and 4.41 ppm) also shift approximately 0.4 ppm downfield, compared to the positions of hydrogen peaks of pure azopolymer to which a metal ion is not bonded ($5^{th}$ hydrogen of FIG. 2a 4H, 3.99 ppm). That is, if azopolymer forms a complex, the hydrogen atoms around the azo group of the azopolymer and the hydrogen atoms in the ethyleneoxy group are de-shielded, and thus, it can be confirmed that a metal ion is bonded to the azo group and ethyleneoxy group of the azopolymer to form a complex.

Referring to FIG. 3b, FIG. 3c, FIG. 4b and FIG. 4c, also in the complex of PDAEMA-S2 or PDAEMA-S3 azopolymer with a different length of ethyleneoxy group and $Li^+$ or $Na^+$ cation, the results coincide with the PDAEMA-S1 azopolymer complex. However, as the length of the ethyleneoxy group to which $Li^+$ or $Na^+$ cation is bonded increases, due to the hydrogen atoms existing in the ethyleneoxy groups, doublet peaks appearing between 4.4 ppm to 3.6 ppm appeared more splitting into quartet or multiplet peaks.

Meanwhile, referring to FIG. 2d, FIG. 3d and FIG. 4d, in case $KPF_6$ metal salts are added to the azopolymer solutions, NMR results identical to the azopolymer to which a metal salt is not added was obtained. Thus, it is confirmed that the azopolymer according to one embodiment of the present invention cannot form a complex with $K^+$ cation released from a $KPF_6$ metal salt, regardless of the length of the ethyleneoxy group.

Experimental Example 5: NMR Evaluation of Azopolymer Complex after UV Irradiation After irradiating UV of 365 nm wavelength to the azopolymer solution according to one embodiment of the present invention and the azopolymer solution into which a metal solution was introduced, $^1$H-NMR spectra were measured.

Referring to the result of Example 1 of Table 2, the ratio of trans-azobenzene and cis-azobenzene existing in the pure azopolymer solution after irradiating UV for 5 minutes is confirmed as 34% to 66%. Thus, referring to FIG. 5a, hydrogen peaks caused by trans-azobenzene weakly appeared at 7.72 ppm ($1^{st}$ and $2^{nd}$ hydrogen), 7.15 ppm ($3^{rd}$ hydrogen), 6.76 ppm ($4^{th}$ hydrogen), and new hydrogen peaks caused by cis-azobenzene appeared as multiplet peaks at 7.01 ppm ($1^{st}$ hydrogen) and 6.73 ppm (2, 3, $4^{th}$ hydrogen). From these results, it is confirmed that a photoisomerization reaction occurred wherein the stable trans structure of azobenzene group is converted into the unstable cis structure by UV.

However, comparing FIG. 5b and FIG. 5c with FIG. 2b and FIG. 2c, in the case of azopolymer PDAEMA-S1 that forms a complex with a $Li^+$ or $Na^+$ cation, the positions and splitting of hydrogen peaks by hydrogen atoms existing in the azobenzene group appeared identically before UV irradiation (FIGS. 2b and 2c) and after UV irradiation (FIG. 5b and FIG. 5c).

From these results, it is confirmed that by the formation of a complex of azopolymer with a $Li^+$ or $Na^+$ cation, the azopolymer chains become rigid and a free volume between the polymer chains decreases, and thus, even if UV is irradiated, a photoisomerization reaction cannot freely occur regardless of the kind of cation. Referring to Table 3 and Table 4, it is confirmed that a photoisomerization reaction occurs little with the maximum 8% or less in the azopolymer complex.

Similarly, the results of irradiating UV after a $LiPF_6$ or $NaPF_6$ metal salt is added to the solution of azopolymer PDAEMA-S2 or PDAEMA-S3 with different ethyleneoxy group length were also identical to the results obtained in the PDAEMA-S1 solution (See FIG. 6b, FIG. 6c, FIG. 7b and FIG. 7c).

Meanwhile, referring to FIG. 5d, in case a $KPF_6$ metal salt is added to the azopolymer PDAEMA-S1, after UV irradiation, $^1$H-NMR spectrum identical to that of pure azopolymer PDAEMA-S1 without a metal salt was obtained. Thus, it is confirmed that the azopolymer PDAEMA-S1 does not form a complex with a $K^+$ cation. Similarly, the results of irradiating UV after adding a $KPF_6$ metal salt to the solution of azopolymer PDAEMA-S2 or PDAEMA-S3 with different ethyleneoxy group length was also identical to the result obtained in PDAEMA-S1 solution (See FIG. 6d and FIG. 7d).

In conclusion, it can be confirmed that $Li^+$ and $Na^+$ cations released from metal salts bond simultaneously with the azo group of azopolymer and the ethyhleneoxy group introduced at the side chain of azopolymer, to form a new complex. And, it can be also confirmed that PDAEMA-S1 of which length of ethyleneoxy group introduced as a ligand is shortest, more strongly bonds with a $Li^+$ or $Na^+$ cation than PDAEMA-S2 or PDAEMA-S3 with relatively long length. The bonding force between the azopolymer and the metal cation derived from the above result was $Li^+>>Na^+>>>K^+$ in order.

From the above experimental results, it can be confirmed that the azopolymer according to one embodiment of the present invention may be applied as a material of a sensor capable of selectively detecting a $Li^+$ or $Na^+$ cation. And, it can be also confirmed that the azopolymer may be applied as a new functional polymer material capable of selectively capturing $Li^+$ and/or $Na^+$ cation from a mixed solution including various alkali metals, heavy metals and/or transition metals, etc.

The invention claimed is:
1. An azomonomer represented by the following Chemical Formula 1:

[Chemical Formula 1]

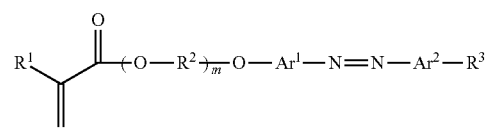

in the Chemical Formula 1, $R^1$ is hydrogen or a methyl group,
$R^2$ is an alkylene group having 1 to 4 carbon atoms,
$R^3$ is an alkyl group having 10 to 16 carbon atoms,
each of $Ar^1$ and $Ar^2$ is independently an arylene group having 6 to 12 carbon atoms, and
m is an integer of 2 to 5.

2. The azomonomer according to claim 1, wherein $R^2$ is an 1,2-ethylene group.

3. The azomonomer according to claim 1, wherein $Ar^1$ and $Ar^2$ are phenylene groups.

4. An azopolymer comprising a repeat unit represented by the following Chemical Formula 2:

[Chemical Formula 2]

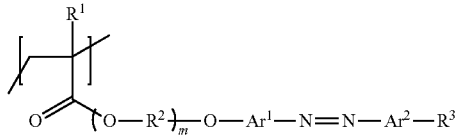

in the Chemical Formula 2, $R^1$ is hydrogen or a methyl group, $R^2$ is an alkylene group having 1 to 4 carbon atoms, $R^3$ is an alkyl group having 10 to 16 carbon atoms, each of $Ar^1$ and $Ar^2$ is independently an arylene group having 6 to 12 carbon atoms, and m is an integer of 2 to 5.

5. The azopolymer according to claim 4, wherein a number average molecular weight is 10,000 to 50,000 g/mol, and a molecular weight distribution is 1.2 to 4.0.

6. The azopolymer according to claim 4, wherein a glass transition temperature is 60° C. to 120° C., a nematic liquid crystalline transition temperature is 90° C. to 160° C., and a melting point is 110° C. to 210° C.

7. A metal ion sensor using the azopolymer according to claim 4.

8. The metal ion sensor according to claim 7, wherein the metal ion sensor detects a lithium ion, a sodium ion or a mixture thereof.

9. A metal ion capturing agent using the azopolymer according to claim 4.

10. The metal ion capturing agent according to claim 9, wherein the metal ion capturing agent captures a lithium ion, a sodium ion or a mixture thereof in a metal ion mixture.

* * * * *